US009689567B2

(12) United States Patent
Starnes (10) Patent No.: US 9,689,567 B2
(45) Date of Patent: Jun. 27, 2017

(54) HANDHELD SURGICAL INSTRUMENT REPAIR STATION WITH ASSOCIATED ALIGNMENT TOOLS

(71) Applicant: Gary Starnes, Waxahachie, TX (US)

(72) Inventor: Gary Starnes, Waxahachie, TX (US)

(*) Notice: Subject to any disclaimer, the term of this patent is extended or adjusted under 35 U.S.C. 154(b) by 0 days.

(21) Appl. No.: 14/843,588

(22) Filed: Sep. 2, 2015

(65) Prior Publication Data

US 2016/0058511 A1 Mar. 3, 2016

Related U.S. Application Data

(60) Provisional application No. 62/044,758, filed on Sep. 2, 2014, provisional application No. 62/164,093, filed on May 20, 2015.

(51) Int. Cl.
*F21V 33/00* (2006.01)
*A61B 19/02* (2006.01)
*A61B 17/28* (2006.01)
*A61B 50/31* (2016.01)
*A61B 50/30* (2016.01)
*A61B 17/00* (2006.01)
*A61B 50/00* (2016.01)
(Continued)

(52) U.S. Cl.
CPC .......... *F21V 33/0068* (2013.01); *A61B 17/28* (2013.01); *A61B 19/0271* (2013.01); *A61B 50/20* (2016.02); *A61B 50/30* (2016.02); *A61B 50/31* (2016.02); *A61B 90/08* (2016.02); *A61B 2017/00526* (2013.01); *A61B 2017/00876* (2013.01); *A61B 2050/0056* (2016.02); *A61B 2050/0076* (2016.02); *A61B 2050/21* (2016.02); *A61B 2090/3616* (2016.02)

(58) Field of Classification Search
CPC ..... A61B 17/28; A61B 19/02; A61B 19/0256; A61B 19/0271; A61B 19/0288; A61B 50/20; A61B 50/30; A61B 50/31; A61B 2017/00876; A61B 2050/0056; A61B 2050/0076; A61B 2050/21; A61B 2090/3616; B65D 85/00; F21V 33/00; F21V 33/0068
USPC ......... 206/363-373, 438, 570-572; 362/154; 422/300
See application file for complete search history.

(56) References Cited

U.S. PATENT DOCUMENTS

4,229,420 A * 10/1980 Smith .................... A61B 50/20
 206/363
4,353,273 A 10/1982 Freberg
(Continued)

*Primary Examiner* — Bryon Gehman
(74) *Attorney, Agent, or Firm* — James E. Walton (57) ABSTRACT

A surgical-instrument alignment station comprises a case having an interior surface and an exterior surface. The case comprised a top side and a bottom side joined along a hinge. A plurality of suction cups are fixed to the exterior surface of the bottom side of the case for allowing the case to be selectively attached to a surface. An alignment block is affixed to the exterior surface of the bottom side of the case. The alignment block comprises an elongated element that defines a plurality of slots for selectively holding a plurality of surgical-tool implements. The elongated element further comprises a clamping element configured to selectively engage surgical-tool implements. The station further comprises a first internal pocket in the top side of the case and a light source in the top side of the case.

14 Claims, 10 Drawing Sheets

(51) Int. Cl.
*A61B 50/20* (2016.01)
*A61B 90/00* (2016.01)

(56) References Cited

U.S. PATENT DOCUMENTS

| | | | | |
|---|---|---|---|---|
| 5,219,446 A * | 6/1993 | Klepac | ............... | B25H 3/02 |
| | | | | 362/154 |
| 5,424,048 A * | 6/1995 | Riley | ............... | A61B 50/31 |
| | | | | 206/370 |
| 5,449,069 A * | 9/1995 | Pijanowski | ........... | A61B 50/20 |
| | | | | 206/370 |
| 5,540,901 A * | 7/1996 | Riley | ............... | A61B 50/31 |
| | | | | 206/370 |
| 5,791,471 A * | 8/1998 | Radmand | ............... | A61C 19/00 |
| | | | | 206/366 |
| 6,267,484 B1 * | 7/2001 | Baker | ............... | A01K 97/06 |
| | | | | 362/154 |
| 6,424,611 B1 * | 7/2002 | Quilling | ............... | G11B 23/505 |
| | | | | 369/72 |
| 6,467,618 B2 * | 10/2002 | High | ............... | B65D 85/00 |
| | | | | 206/370 |
| 7,441,660 B2 * | 10/2008 | Caron | ............... | A61B 50/30 |
| | | | | 206/370 |
| 7,748,529 B2 * | 7/2010 | Foreman | ............... | A61B 50/30 |
| | | | | 206/370 |
| 7,967,137 B2 * | 6/2011 | Fulbrook | ............... | A61B 50/33 |
| | | | | 206/370 |
| 8,001,640 B2 | 8/2011 | Carter | | |
| 8,685,068 B2 * | 4/2014 | Sixto | ............... | A61B 17/8014 |
| | | | | 206/363 |
| 9,072,543 B2 * | 7/2015 | Miller | ............... | A61B 50/20 |
| 9,084,593 B2 * | 7/2015 | Yakel | ............... | A61B 19/0271 |
| 9,259,272 B2 * | 2/2016 | Ramkhelawan | ....... | A61B 50/20 |
| 2011/0042253 A1 * | 2/2011 | Levine | ............... | A61B 50/362 |
| | | | | 206/366 |
| 2014/0262881 A1 * | 9/2014 | Colby | ............... | A61B 19/0288 |
| | | | | 206/363 |

* cited by examiner

HANDHELD SURGICAL INSTRUMENT REPAIR STATION WITH ASSOCIATED ALIGNMENT TOOLS

CROSS REFERENCE TO RELATED APPLICATIONS

This application claims the benefit of U.S. Provisional Application No. 62/044,758, filed Sep. 2, 2014, and of U.S. Provisional Application No. 62/164,093, filed May 20, 2015, both of which are hereby incorporated herein by reference for all purposes as if fully set forth herein.

TECHNICAL FIELD

The present disclosure relates generally to systems and methods associated with receptacles configured for holding and repairing a particular set of articles, and more particularly to systems and methods associated with receptacles configured for holding surgical-instrument alignment tools and for repairing surgical instruments.

BRIEF DESCRIPTION OF THE DRAWINGS

Features, aspects, and embodiments of the present disclosure are described in conjunction with the attached drawings, in which:

FIGS. 6-8 show clarifying views of an embodiment of the box lock spreading pliers, where

Where used in the various figures of the drawings, the same reference numerals designate the same or similar parts. Furthermore, when the terms "front," "back," "first," "second," "upper," "lower," "height," "top," "bottom," "outer," "inner," "width," "length," "end," "side," "horizontal," "vertical," and similar terms are used herein, it should be understood that these terms have reference only to the structure shown in the drawing and are utilized only to facilitate describing embodiments of the present disclosure.

All figures are drawn for ease of explanation of the basic teachings of the present disclosure only; the extensions of the figures with respect to number, position, relationship, and dimensions of the parts will either be explained or will be within the skill of persons of ordinary skill in the art after the following teachings of the present disclosure have been read and understood. Further, the exact dimensions and dimensional proportions to conform to specific width, length, and similar requirements will likewise be within the skill of the art after the following teachings of the present disclosure have been read and understood.

Embodiments of the system for repairing surgical instruments according to the present disclosure will now be described in detail with reference to the accompanying drawings.

DESCRIPTION OF THE PREFERRED EMBODIMENT

Figure 1:
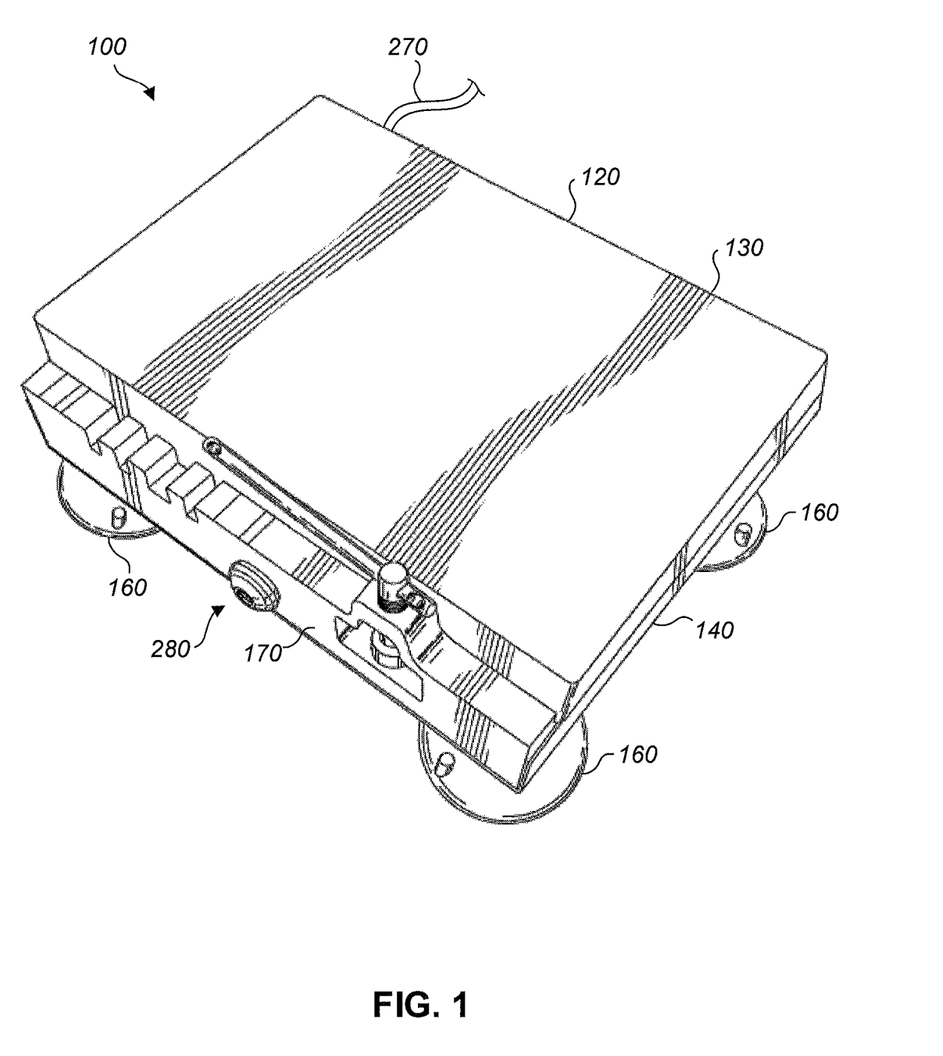
FIG. 1 shows a perspective view of a surgical-instrument alignment station in a closed configuration.
Figure 2:
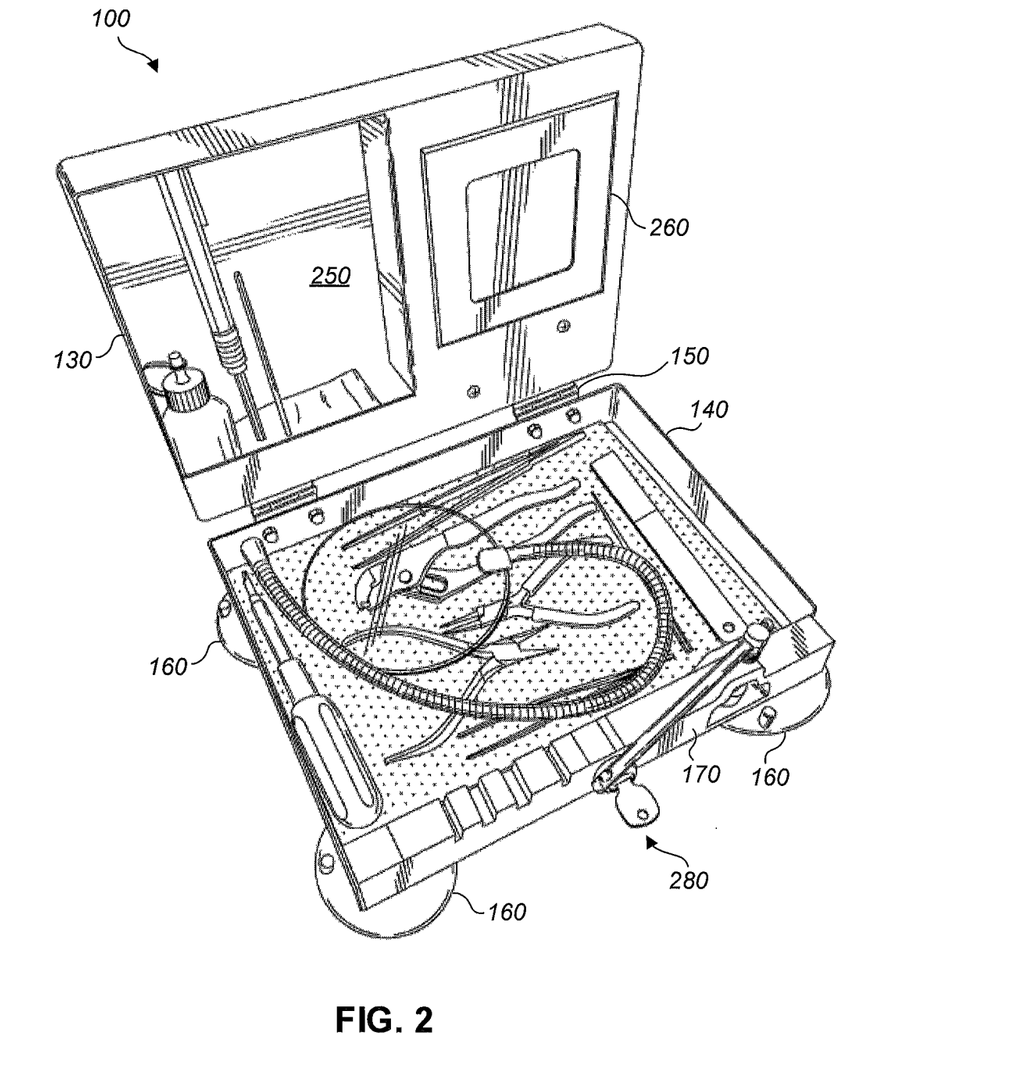
FIG. 2 shows a perspective view of the surgical-instrument alignment station shown in FIG. 1 in an open configuration with a magnifier stowed.
Figure 3:
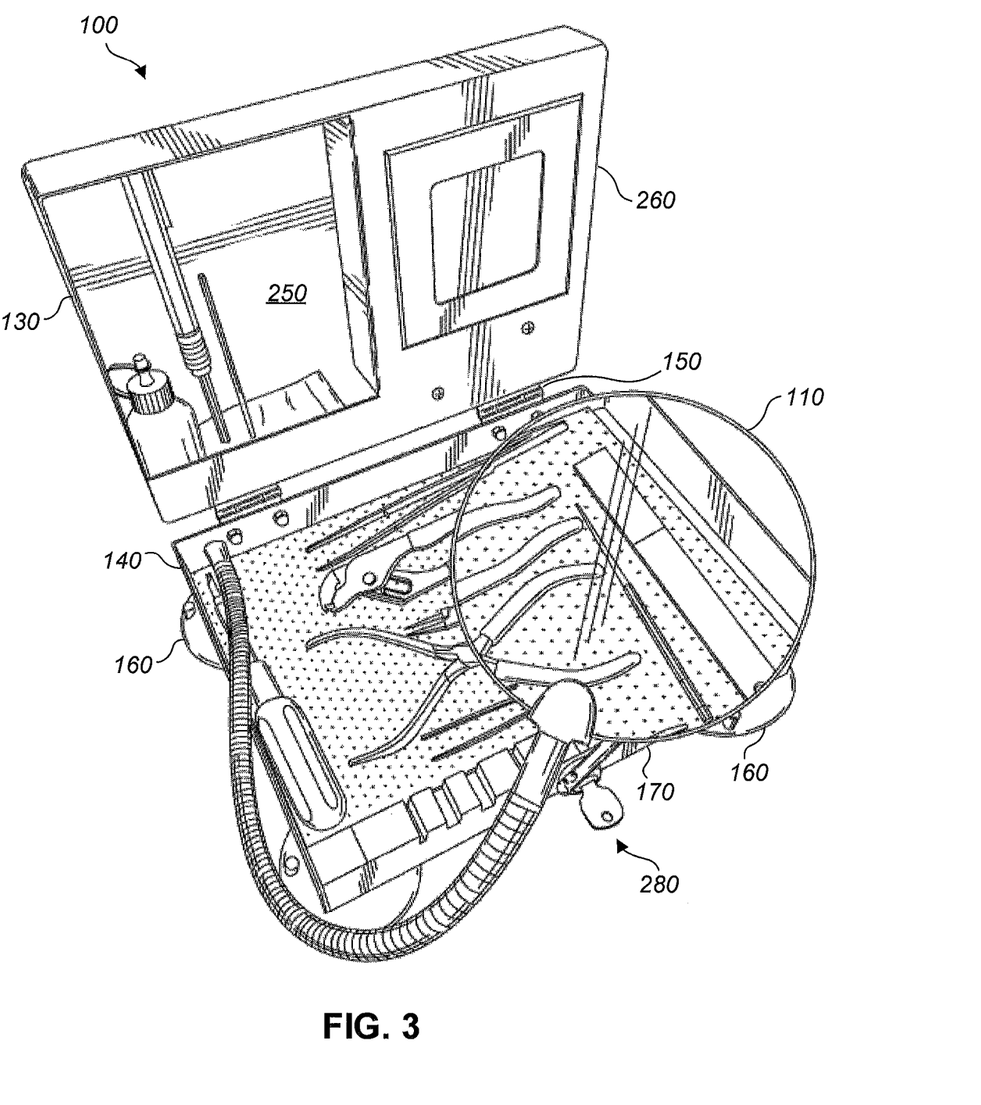
FIG. 3 shows a perspective view of the surgical-instrument alignment station shown in FIG. 1 in an open configuration with the magnifier deployed for use.

Referring to FIGS. 1-3, perspective views of a surgical-instrument alignment station 100 are shown. FIG. 1 shows the station 100 in a closed configuration. FIG. 2 shows the station 100 in an open configuration with a magnifier 110 stowed. FIG. 3 shows the station 100 in an open configuration with the magnifier 110 deployed for use. As a result, the portion of the view seen through the magnifier 110 in FIG. 3 is enlarged to illustrate the magnifying effect of the magnifier 110.

The station 100 comprises a case 120 having an interior surface and an exterior surface. The case 120 comprises a top side 130 and a bottom side 140 joined along one or more hinges 150. The case 120 can include securing elements, such as the illustrated plurality of suction cups 160 that are fixed to the exterior surface of the bottom side 140 of the case 120 for allowing the case 120 to be selectively attached to a surface. Alternatively, the case 120 can be attached to another surface using hardware, adhesives, or hook and loop fasteners (such as Velcro® fasteners). The case 120 can be formed of a rigid material, such as metal or plastic. For example, the case 120 can be formed of stainless steel. The magnifier 110 is fixed to the bottom side of the case 120 and includes a flexible shaft that allows it to be selectively positioned by an end user.

Figure 4:
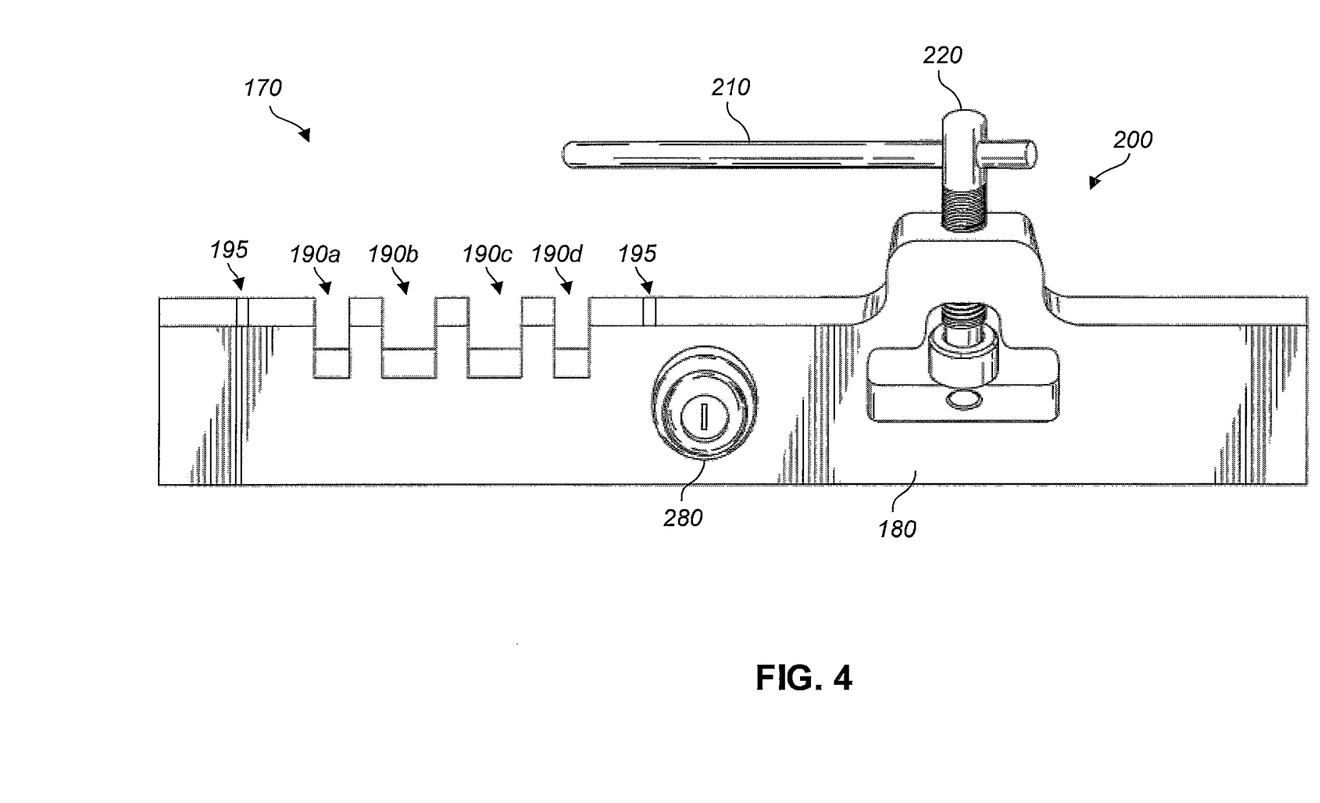
FIG. 4 shows an isolated front view of the alignment block.

An alignment block 170 is fixed to the exterior surface of the bottom side 140 of the case 120. FIG. 4 shows an isolated front view of the alignment block 170 for the sake of improved clarity. The alignment block 170 comprises an elongated element 180 that defines a plurality of slots 190a, 190b, 190c, and 190d for selectively holding a plurality of surgical-tool implements during alignment procedures. In some embodiments, the slots 190a-190d can include slots of varying widths. For example, slot 190a can have a first width and slot 190b can have a second width, where the first width is different from the second width. The alignment block 170 can also include one or more indicia 195 thereon, each being suitable for use as a calibration gauge. For example, the indicia 195 can be configured for quickly checking for proper spacing between the jaws of tissue forceps.

Figure 5:
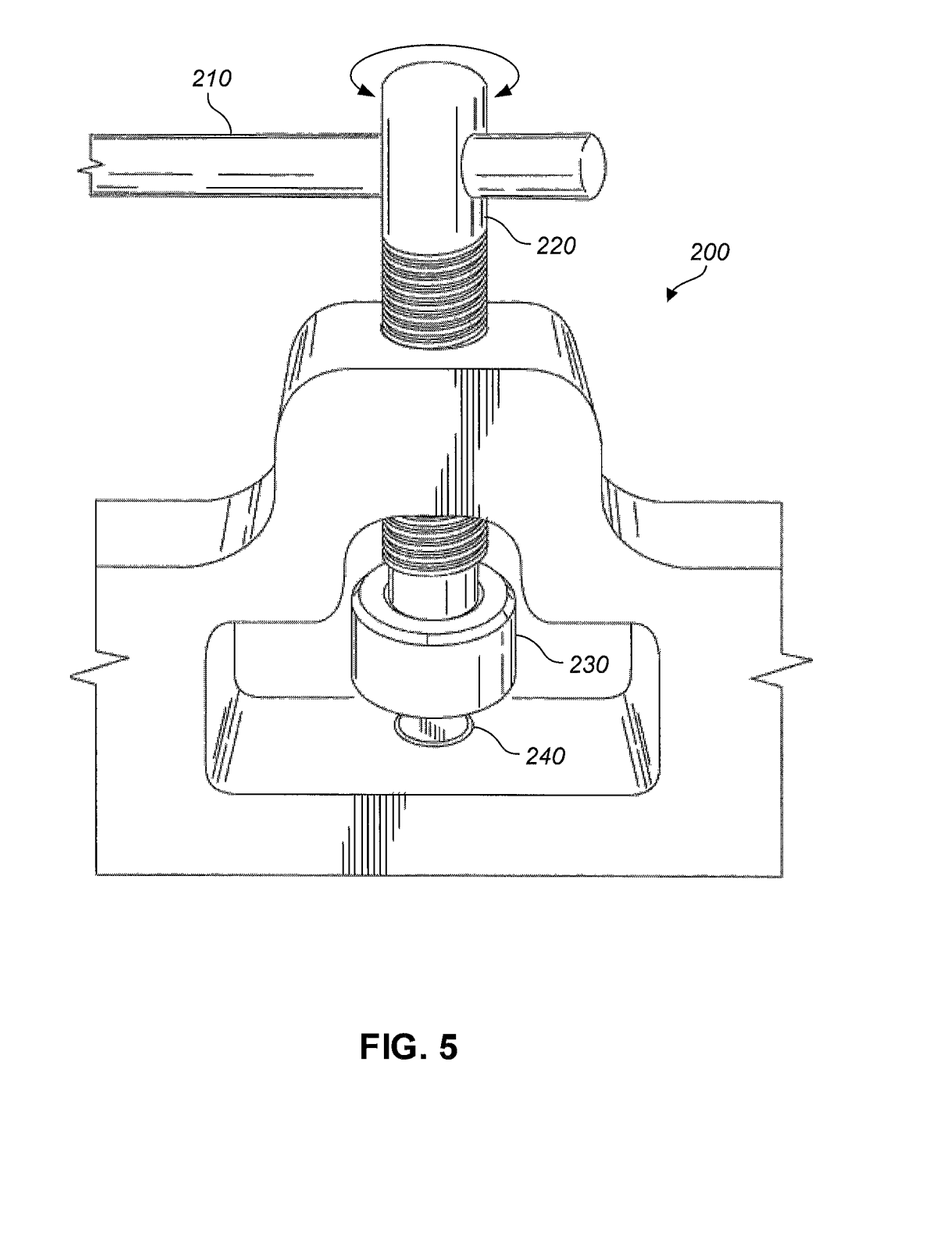
FIG. 5 shows an isolated front view of the clamping element.
Figure 9:
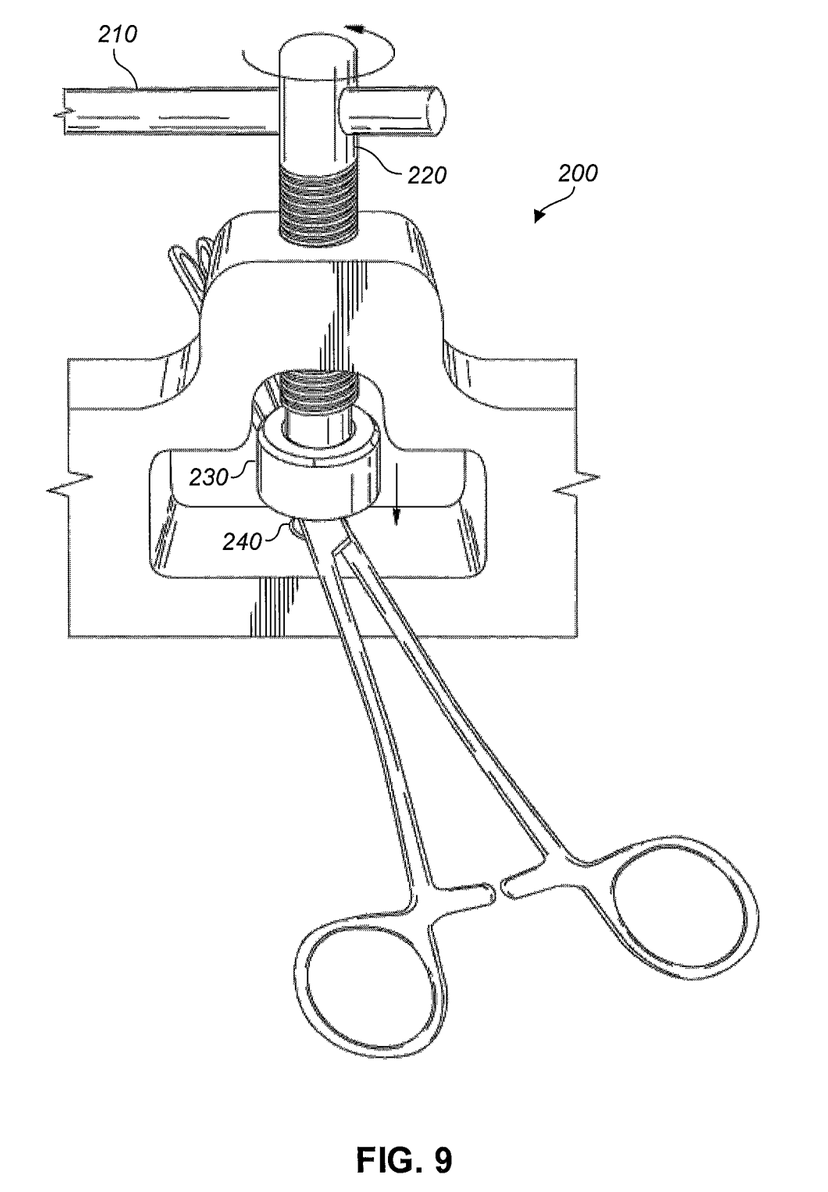
FIG. 9 shows a view of forceps in the clamping element.

The elongated element 180 further comprises a clamping element 200, which constitutes an example of a screw press, configured to selectively engage said surgical-tool implements. FIG. 5 shows an isolated front view of the clamping element 200 for the sake of improved clarity. The clamping element 200 includes a handle 210 connected to a threaded shaft 220. An end-user can rotate the handle 210 in order to raise or lower the threaded shaft 220 and a clamping element 230 connected thereto relative to the elongated element 180 of the alignment block 170. A magnetic element 240 is fixed to the elongated element 180 of the alignment block 170. The magnetic element 240 is axially aligned with the threaded shaft 220. As shown in FIG. 9, the magnetic element 240 can be used for securing a surgical-tool implement while the implement is being clamped by the clamping element 200.

Referring back to FIGS. 1-3, the top side 130 of the case 120 comprises an internal pocket 250 and a light source 260. In some embodiments, the light source 260 can comprise a removable battery-powered lighting element that can be completely separated from the case 120 by an end-user. In some embodiments, the case 120 can include an electrical power cord 270 for providing electrical power from an external power source (not shown), such as a wall outlet, to the light source 260. For some embodiments, the electrical power cord 270 can be, for example, an electrical power cord that complies with environmental standards in which the station 100 may be used, such as hospital standards.

In some embodiments, the case 120 can further include a means for allowing an end user to secure the case 120 in the closed configuration shown in FIG. 1. For example, the case 120 can include a key lock 280. Alternatively, any other type of lock can be used, including a combination lock. In some embodiments, the case 120 can be provided with a hasp or other such means for allowing an end-user to secure the case 120 in the closed configuration using a separate lock, such as a pad-lock.

The case 120 includes storage space therein for storing a variety of tools. For example, the tools can include lubricants, pliers, files, spreading/cleaning tools, buffing and deburring tools, screwdrivers, and cleaning pads.

The lubricants can include any of a variety of widely known liquid and solid lubricants. For example, the lubricants can include instrument milk, which is a concentrated lubricant that can be applied to surgical instruments to loosen sticking or stiff joints.

The pliers can include chain-nose pliers, which are pliers that have a flat inner jaw surface and can be used to firmly grasp specific parts of bent surgical instruments so they can be bent back to the correct operating position. The pliers can also include round-nose pliers, which are pliers having two cone-shaped jaws and can be used to reshape bent skin hooks. For example, the round nose can be used to reshape the curved tip of a skin hook to its original or desired position.

The files can include a triangle file, which is a triangle-shaped file that can be used to remove metal from surgical instruments. A triangle file can also be used to restore the teeth on tissue forceps and the teeth on the jaws of ring forceps. A triangle file can also be used to remove burrs. In some embodiments, a triangle file can be configured to remove metal only when pushed in one particular direction. The files can also include a point file, which is a file that has a specially designed slot running the length of the file that can be used in a first sharpening stage to sharpen and restore the shape of the points of skin hooks, rake retractors, towel clips, and other sharp-point instruments.

The spreading/cleaning tools can include a multi-tipped tool having a reversible tip that can be extremely sharp and can be used to clean impacted material from the teeth of instruments and to separate misaligned teeth of standard- and micro-tissue forceps and Ocshner forceps.

The buffing and deburring tools can include a three-stage buffing and deburring stick, which is a tool that can have plural buffing surfaces and can be used to restore the finish to stainless instruments. For example, in some embodiments it can have three grits that are identifiable by their respective different colors, for example Pink=Course, White=Medium, Gray=Fine. The plural stages of polishing can be used to restore the finish to the points of instruments after reshaping with the point file. The buffing and deburring tool can also to be used to remove scratches that may affect instrument function.

The screwdrivers can include any of a variety of widely-known types of screwdrivers. For example, the screwdrivers can include a slotted screwdriver that can be sued to tighten or loosen screws on a surgical instrument.

The cleaning pads can include various abrasive and non-abrasive towels, sponges, or pads. For example, the cleaning pads can include abrasive pads, such as Scotch-Brite® scouring pads, that can be used on stainless instruments to remove scratches and refinish the surface of surgical instruments to a satin finish.

Figure 6:
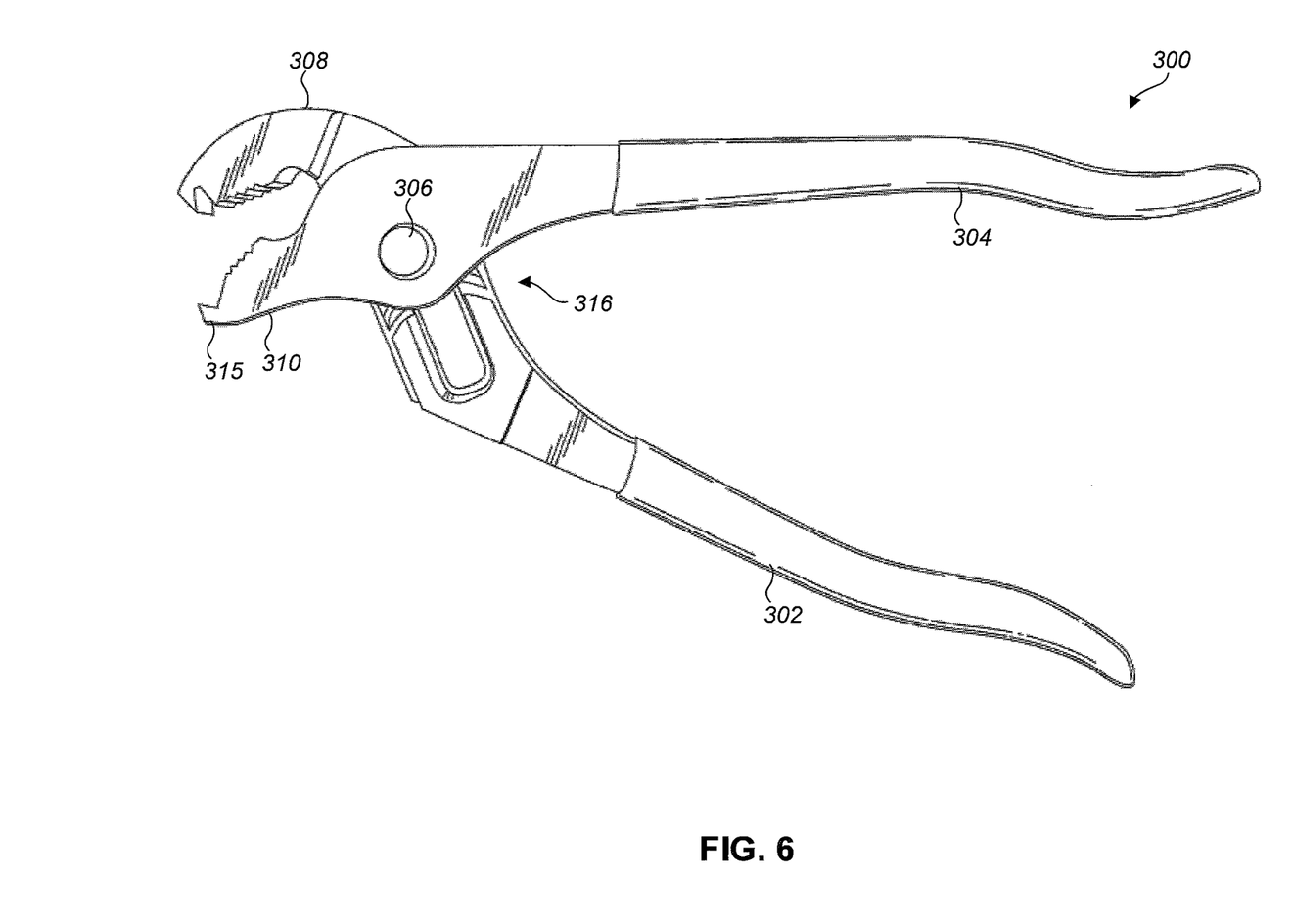
FIG. 6 shows a perspective view of the notched pliers.
Figure 7A:
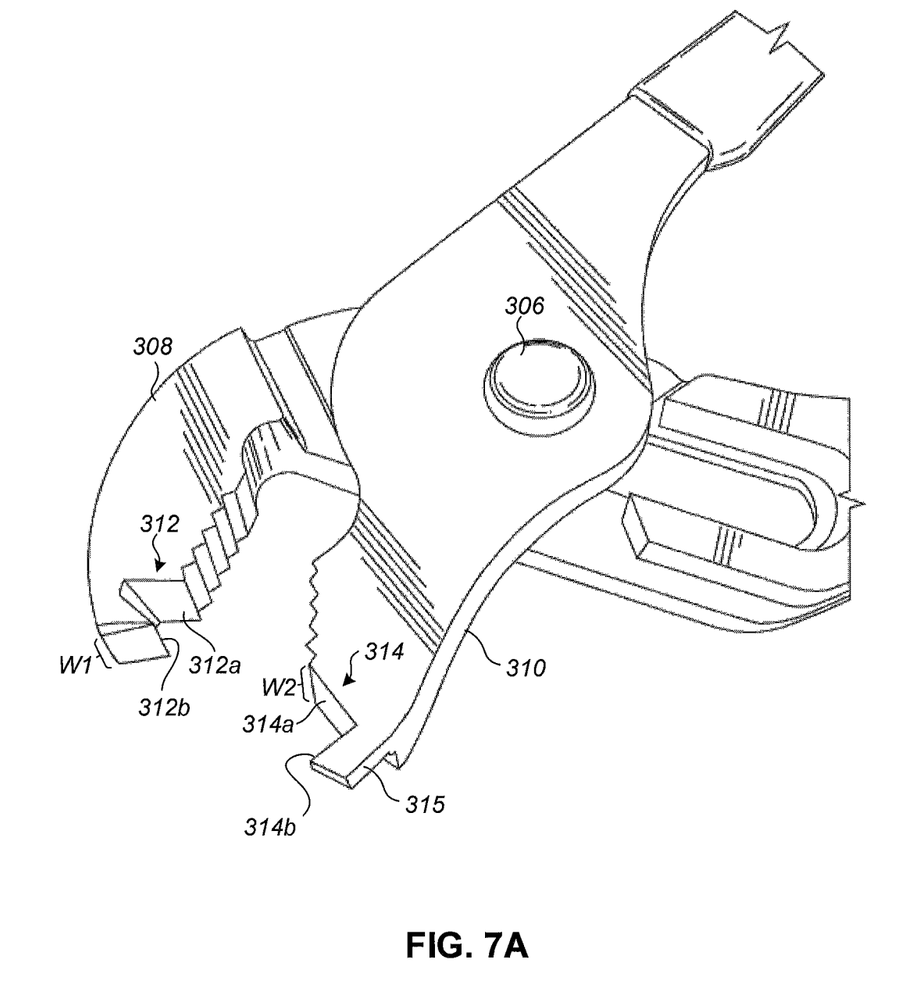
FIGS. 7A and 7B show respective close-up views of respective sides of the gripping end of the pliers.
Figure 7B:
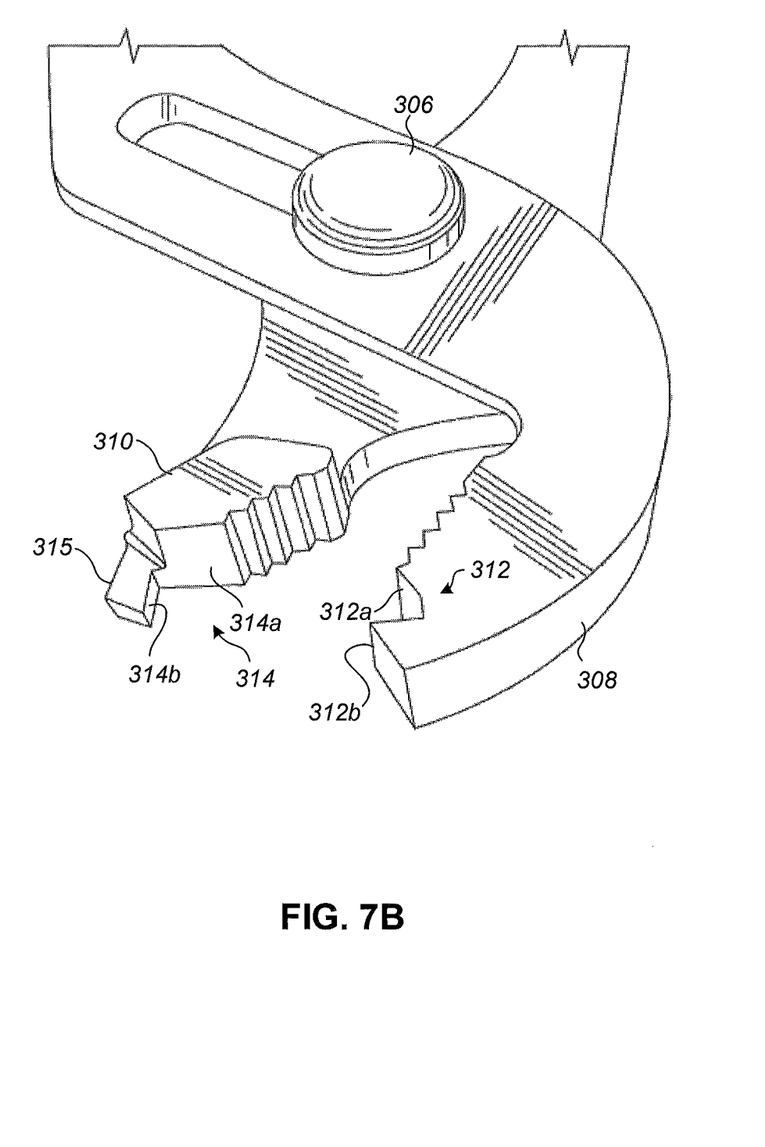
Figure 8:
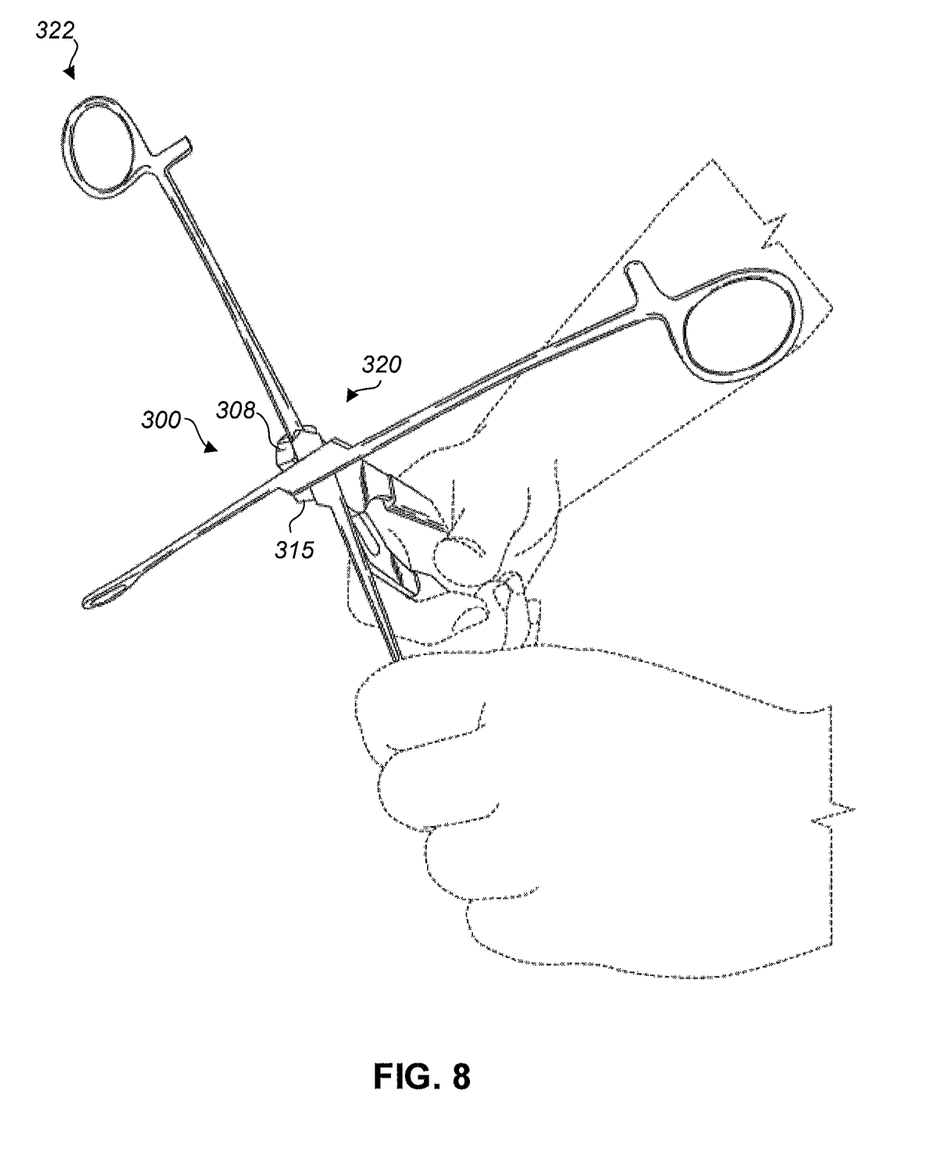
FIG. 8 shows a view of the notched pliers being used to adjust the box joint of a pair of forceps.

The pliers can also include box-lock spreading pliers 300 shown in FIGS. 6-8. The pliers 300 can be adjustable and can have two specially designed teeth in the jaw that are used to spread a stiff box lock after instrument milk lubrication does not eliminate the stiffness.

The box-lock spreading pliers 300 includes a pair of opposed handle grips 302 and 304 which define pliers lever arms connected through a pivot axis or pin 306. The pliers 300 include an upper jaw 308 and a lower jaw 310. Each jaw 308 and 310 includes a notched opposed portion 312 and 314 respectively. The upper and lower jaws 308 and 310 can be adjusted relative to each other using a slotted-adjustment mechanism 316.

The jaw 308 includes a first notched portion 312 comprising substantially planar surfaces 312*a* and 312*b* that each extends approximately equal to the width W1 of the upper jaw 308. The lower jaw 310 includes a second notched portion 314 comprising substantially planar surfaces 314*a* and 314*b*. The planar surface 314*a* extends approximately equal to the width W2 of the lower jaw 310, while the planar surface 314*b* extends approximately equal to, or less than, one-half of the width W2 of the lower jaw 310. The planar surface 314*b* is an inner surface of a narrow tine portion 315 located at the distal end of the jaw 310. The narrow tine portion 315 has a width W2 that is less than or equal to the width W1 of the opposing jaw 308. The widths W1 and W2 can be substantially equal or can differ. The notched portions 312 and 314 are adapted to engage an open box lock portion of a surgical tool, for example to aid in adjustment of a box lock such as the box lock portion 320 of a surgical tool 322 as shown in FIG. 8.

While various embodiments in accordance with the disclosed principles have been described above, it should be understood that they have been presented by way of example only, and are not limiting. Thus, the breadth and scope of the invention(s) should not be limited by any of the above-described exemplary embodiments, but should be defined only in accordance with the claims and their equivalents issuing from this disclosure. Furthermore, the above advantages and features are provided in described embodiments, but shall not limit the application of such issued claims to processes and structures accomplishing any or all of the above advantages.

Additionally, the section headings herein are provided for consistency with the suggestions under 37 C.F.R. 1.77 or otherwise to provide organizational cues. These headings shall not limit or characterize the invention(s) set out in any claims that may issue from this disclosure. Specifically and by way of example, although the headings refer to a "Technical Field," such claims should not be limited by the language chosen under this heading to describe the so-called technical field. Further, a description of a technology in the "Background" is not to be construed as an admission that technology is prior art to any invention(s) in this disclosure. Neither is the "Summary" to be considered as a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings set forth herein.

What is claimed is:

1. A surgical-instrument alignment station, comprising:
a case having an interior surface and an exterior surface, wherein said case comprises a top side and a bottom side joined along a hinge;
a securing element for allowing the case to be selectively attached to a surface; and
an alignment block affixed to the exterior surface of the bottom side of the case, the alignment block comprising an elongated element that defines a plurality of slots for selectively holding a plurality of surgical-tool implements, and said elongated element further comprising a clamping element configured to selectively engage the surgical-tool implements wherein said clamping element is adjustable.

2. The alignment station of claim 1, further comprising a light source in the top side of the case.

3. The alignment station of claim 2, wherein the light source comprises a removable battery-powered lighting element.

4. The alignment station of claim 2, further comprising an electrical power cord for providing electrical power from an external power source to the light source.

5. The alignment station of claim 1, wherein the case includes stainless steel.

6. The alignment station of claim 1, further comprising a locking mechanism for locking the top side and the bottom side together in a closed configuration.

7. The alignment station of claim 1, further comprising a magnifying element fixed to the case wherein the magnifying element includes a flexible shaft that allows said magnifying element to be selectively positioned.

8. The alignment station of claim 1, wherein the plurality of slots of the alignment block include a first slot having a first width and a second slot having a second width that is different from the first width.

9. The alignment station of claim 1, wherein the alignment block further comprises an indicia thereon suitable for use as a calibration gauge.

10. The alignment station of claim 1, further comprising storage space within the case.

11. The alignment station of claim 10, further comprising box-lock-spreading pliers stored in said storage space.

12. The alignment station of claim 10, further comprising at least one of a plier, a file, a lubricant, and a multi-stage buffing and deburring stick stored in said storage space.

13. The alignment station of claim 1, wherein the securing element includes a plurality of suction cups fixed to the exterior surface of the bottom side of the case.

14. The alignment station of claim 1, further comprising a first internal pocket in the top side of the case.

* * * * *